United States Patent
Yin

(10) Patent No.: US 10,969,864 B2
(45) Date of Patent: Apr. 6, 2021

(54) METHOD, APPARATUS AND DEVICE FOR DETECTING FATIGUE STATE

(71) Applicant: SHENZHEN GOODIX TECHNOLOGY CO., LTD., Shenzhen (CN)

(72) Inventor: Guochao Yin, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 50 days.

(21) Appl. No.: 16/454,014

(22) Filed: Jun. 26, 2019

(65) Prior Publication Data
US 2020/0050266 A1 Feb. 13, 2020

Related U.S. Application Data

(63) Continuation of application No. PCT/CN2018/099250, filed on Aug. 7, 2018.

(51) Int. Cl.
*G06F 3/01* (2006.01)
*G06T 7/00* (2017.01)

(52) U.S. Cl.
CPC ............ *G06F 3/013* (2013.01); *G06T 7/0014* (2013.01); *G06F 2203/011* (2013.01); *G06T 2207/10028* (2013.01); *G06T 2207/30041* (2013.01)

(58) Field of Classification Search
CPC .. G06F 3/013; G06F 2203/011; A61B 5/1103; G08B 21/043; G08B 21/0461;
(Continued)

(56) References Cited

U.S. PATENT DOCUMENTS

2008/0232694 A1* 9/2008 Sulatycke ............... G06T 15/08
382/224
2010/0245093 A1* 9/2010 Kobetski ............ G06K 9/00597
340/576
(Continued)

FOREIGN PATENT DOCUMENTS

CN 101803928 A 8/2010
CN 103700217 A 4/2014
(Continued)

OTHER PUBLICATIONS

The Chinese International Search Report of corresponding international application No. PCT/CN2018/099250, dated Dec. 10, 2018.
(Continued)

*Primary Examiner* — Brenda C Bernardi
(74) *Attorney, Agent, or Firm* — J.C. Patents

(57) ABSTRACT

The present disclosure provides a method, an apparatus and a device for detecting a fatigue state. In this method, by receiving an initial image sent by a 3D sensor, where the initial image includes depth information containing an eye contour, extracting eye state information from the initial image, and determining whether a user is currently in the fatigue state according to the eye state information, detecting whether the user is in the fatigue state through the eye state information is thereby achieved, with high detection efficiency and more accurate detection results.

18 Claims, 8 Drawing Sheets

(58) Field of Classification Search
CPC ...... G08B 21/0476; G08B 21/06; G06K 9/00; G06T 7/0014; G06T 2207/10028; G06T 2207/30041
See application file for complete search history.

(56) References Cited

U.S. PATENT DOCUMENTS

| | | | |
|---|---|---|---|
| 2012/0002843 A1* | 1/2012 | Yoda | B60K 28/06 |
| | | | 382/103 |
| 2012/0219189 A1 | 8/2012 | Wu et al. | |
| 2018/0140187 A1* | 5/2018 | Watanabe | G06K 9/00604 |
| 2019/0320890 A1* | 10/2019 | Tahara | G06K 9/0061 |

FOREIGN PATENT DOCUMENTS

| | | |
|---|---|---|
| CN | 106485880 A | 3/2017 |
| CN | 106943263 A | 7/2017 |
| EP | 2 237 237 A1 | 10/2010 |
| EP | 3 326 513 A1 | 5/2018 |
| JP | 2005-312868 A | 11/2005 |

OTHER PUBLICATIONS

The extended European Search Report, including Supplemental Search Report of corresponding European application No. 18893338.6-1206, dated Feb. 4, 2020.

* cited by examiner

METHOD, APPARATUS AND DEVICE FOR DETECTING FATIGUE STATE

CROSS-REFERENCE TO RELATED APPLICATIONS

This application is a continuation of International Application No. PCT/CN2018/099250, filed on Aug. 7, 2018, which is herein incorporated by reference in its entirety.

TECHNICAL FIELD

The present disclosure relates to the field of electronic technologies, and in particular, to a method, an apparatus and a device for detecting a fatigue state.

BACKGROUND

When a user is in a fatigue state, the attention of the user may be dispersed and the strain capacity may be lowered. For example, the speed of observing and reacting to the road condition and the surrounding environment will significantly slow down when the user is in a state of fatigue driving, and lack of appropriate rest will increase the possibility of causing a traffic accident. Therefore, it is necessary to detect the fatigue state of the user and remind the user timely.

At present, generally whether a user is currently in the fatigue state is determined by detecting information such as heart rates and behaviors of a human body via a wearable electronic device and then comparing the detected information with a preset index.

However, detection efficiency in this way is low, which requires the user to keep wearing the electronic device for a certain period of time, and the detection result is easily interfered by external factors, thus the detection accuracy is low.

SUMMARY

The present disclosure provides a method, an apparatus and a device for detecting a fatigue state, to achieve to detect whether a user is in a fatigue state through eye state information, which has high detection efficiency and more accurate detection results.

In a first aspect, the present disclosure provides a method for detecting a fatigue state, including:
receiving an initial image sent by a 3D sensor;
extracting eye state information from the initial image; and
determining whether a user is currently in the fatigue state according to the eye state information.

Optionally, the extracting eye state information from the initial image includes:
identifying a first eye region image from the initial image; and
extracting a corneal curvature from the first eye region image, if the eyelid in the first eye region image is in an open state.

Optionally, after identifying the first eye region image from the initial image, the method further includes:
receiving a new initial image sent by the 3D sensor after waiting a first preset time, if the eyelid in the first eye region image is in a closed state;
identifying a second eye region image from the new initial image;
extracting the corneal curvature from the second eye region image, if the eyelid in the second eye region image is in the open state;
continuously obtaining initial images of N frames within a second preset time range according to a preset time interval, if the eyelid in the second eye region image is in the closed state, N being a natural number greater than 1; and
obtaining eye state information within the second preset time range from the initial images of N frames, where the eye state information includes: blink times, total duration of closing eyes, duration of keeping eyes closed, and the corneal curvature.

Optionally, before the determining whether a user is currently in the fatigue state according to the eye state information, the method further includes:
determining whether the corneal curvature is within a preset angle range, and if the corneal curvature is within the preset angle range, taking the corneal curvature as a target corneal curvature;
if the corneal curvature is not within the preset angle range, determining the corneal curvature to be invalid data, and receiving an initial image sent by the 3D sensor again.

Optionally, the determining whether a user is currently in the fatigue state according to the eye state information includes:
comparing the target corneal curvature with a reference corneal curvature, and determining that the user is currently in the fatigue state if an absolute value of a difference between the target corneal curvature and the reference corneal curvature is greater than a preset threshold value.

Optionally, the reference corneal curvature is a corneal curvature detected when the user is in a normal state, or is a pre-stored corneal curvature.

Optionally, the determining whether a user is currently in the fatigue state according to the eye state information further includes:
determining that the user is currently in the fatigue state if at least one of preset conditions is met within the second preset time range, where the preset conditions include:
the blink times being not within a preset amount range;
the total duration of closing eyes being greater than a first upper limit value;
the duration of keeping eyes closed being greater than a second upper limit value;
and
an absolute value of a difference between a corneal curvature of an initial image of at least one frame in the initial images of N frames and the reference corneal curvature being greater than a preset threshold value.

Optionally, before receiving an initial image sent by the 3D sensor, the method further includes:
transmitting a control signal to the 3D sensor to enable the 3D sensor to collect the initial image at a preset frequency.

Optionally, after determining whether a user is currently in the fatigue state according to the eye state information, the method further includes:
transmitting reminding information to the user to remind the user to have a rest if it is determined that the user is currently in the fatigue state.

In a second aspect, the present disclosure provides an apparatus for detecting a fatigue state, including:
a receiving module, configured to receive an initial image sent by a 3D sensor;
an extracting module, configured to extract eye state information from the initial image; and a determining module, configured to determine whether a user is currently in the fatigue state according to the eye state information.

Optionally, the extracting module is specifically configured to:

identify a first eye region image from the initial image; and extract a corneal curvature from the first eye region image, if an eyelid in the first eye region image is in an open state.

Optionally, the extracting module is further configured to:

receive a new initial image sent by the 3D sensor after waiting a first preset time, if the eyelid in the first eye region image is in a closed state;

identify a second eye region image from the new initial image;

extract the corneal curvature from the second eye region image, if the eyelid in the second eye region image is in the open state;

continuously obtain initial images of N frames within a second preset time range according to a preset time interval, if the eyelid in the second eye region image is in the closed state, N being a natural number greater than 1; and obtain eye state information within the second preset time range from the initial images of N frames, where the eye state information includes: blink times, total duration of closing eyes, duration of keeping eyes closed, and the corneal curvature.

Optionally, the apparatus further includes:

a filtering module, configured to determine whether the corneal curvature is within a preset angle range before the determine whether a user is currently in the fatigue state according to the eye state information, take the corneal curvature as a target corneal curvature if the corneal curvature is within the preset angle range, and determine the corneal curvature to be invalid data and receive again an initial image sent by the 3D sensor, if the corneal curvature is not within the preset angle range.

Optionally, the determining module is specifically configured to:

compare the target corneal curvature with a reference corneal curvature, and determine that the user is currently in the fatigue state if an absolute value of a difference between the target corneal curvature and the reference corneal curvature is greater than a preset threshold value.

Optionally, the reference corneal curvature is a corneal curvature detected when the user is in a normal state, or is a pre-stored corneal curvature.

Optionally, the determining module is further configured to:

determine that the user is currently in the fatigue state if at least one of preset conditions is met within the second preset time range, where the preset conditions include:

the blink times being not within a preset amount range;

the total duration of closing eyes being greater than a first upper limit value;

the duration of keeping eyes closed being greater than a second upper limit value;

and an absolute value of a difference between a corneal curvature of an initial image of at least one frame in the initial images of N frames and the reference corneal curvature being greater than a preset threshold value.

Optionally, the apparatus further includes:

a transmitting module, configured to transmit a control signal to the 3D sensor before the initial image sent by the 3D sensor is received, so that the 3D sensor collects the initial image at a preset frequency.

Optionally, the transmitting module is further configured to, after whether the user is currently in the fatigue state is determined according to the eye state information, and if it is determined that the user is currently in the fatigue state, transmit reminding information to the user to remind the user to have a rest.

In a third aspect, the present disclosure provides a wake-up device for an operating system, including:

a 3D sensor and a Microcontroller Unit (MCU), where the 3D sensor is electrically connected with the Microcontroller Unit (MCU);

the 3D sensor is configured to collect an initial image and transmit the initial image to the MCU;

the MCU is configured to perform any one of the fatigue state detection methods according to the first aspect.

In a fourth aspect, the present disclosure provides a wake-up device for an operating system, including:

a memory, used to store a program;

a processor, used to execute the program stored in the memory, where the processor is configured to perform any one of the methods of the first aspect when the program is executed.

In a fifth aspect, the present disclosure provides a computer readable storage medium, including: instructions that cause a computer to perform any one of the methods of the first aspect when the instructions are executed on a computer.

With the method, apparatus and device for detecting fatigue state provided by the present disclosure, an initial image sent by a 3D sensor is received, where the initial image includes depth information containing an eye contour; eye state information is extracted from the initial image; whether a user is currently in a fatigue state is determined according to the eye state information. Thus detecting whether a user is in a fatigue state through eye state information is achieved, with high detection efficiency and more accurate detection results.

BRIEF DESCRIPTION OF THE DRAWINGS

In order to more clearly illustrate the technical solutions in the embodiments of the present disclosure or in the prior art, a brief introduction of the drawings used for describing the embodiments or the prior art will be made below. Obviously, the drawings in the following description show some embodiments of the present disclosure, and those skilled in the art may still derive other drawings from these drawings without any creative effort.

Figure 1:
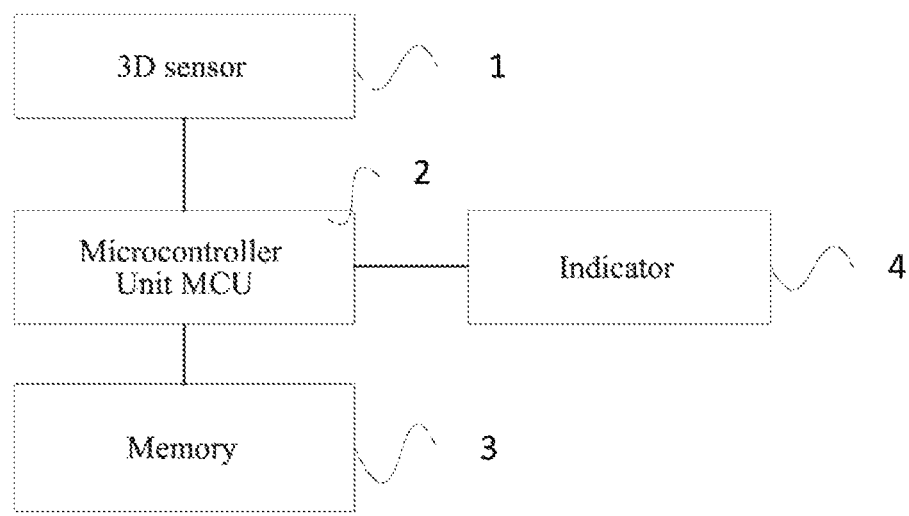
FIG. 1 is a schematic structural diagram of an application scenario according to the present disclosure.

The specific embodiments of the present disclosure have been shown through the above drawings, and more detailed description will be given below. The drawings and texts are not intended to limit the scope of the present disclosure in any way, but to describe the concepts mentioned in the present disclosure for those skilled in the art by referring to the specific embodiments.

DESCRIPTION OF EMBODIMENTS

To make the purposes, technical solutions and advantages of the embodiments of the present disclosure clearer, the technical solutions in the embodiments of the present disclosure will be clearly and completely described below with reference to the drawings in the embodiments of the present disclosure. Apparently, the described embodiments are some but not all of the embodiments according to the present disclosure. All other embodiments obtained by a person of ordinary skill in the art based on the embodiments of the present disclosure without creative efforts fall within the protection scope of the present disclosure.

Terms "first", "second", "third", "fourth" and the like (if any) in the specification and the claims of the present disclosure and in the drawings described above are used to distinguish similar objects rather than describe a specific order or sequence. It should be understood that data used in this way is interchangeable where appropriate so that the embodiments of the disclosure described herein can be implemented in a sequence other than those illustrated or described herein. Moreover, terms "including", "comprising" and "having" and any variations thereof are intended to reference a non-exclusive inclusion. For example, a process, method, system, product, or device that includes a series of steps or units is not necessarily limited to those steps or units that are clearly listed, but may include steps or units that are not clearly listed or that are inherent to such process, method, product or device.

The technical solutions of the present disclosure will be described in detail below by specific embodiments. The following specific embodiments may be combined with each other, and same or similar concepts or processes may not be repeated in some embodiments.

Some terms in the present disclosure will be explained below to facilitate understanding by those skilled in the art.

1) Three Dimensions (3D) is a concept of space, and the three dimensions of a space can be characterized with three axes of X, Y and Z.

2) A 3D sensor is a sensor which not only obtains a plane image of an object, but also obtains depth information of the object. A common 3D sensor includes a 3D camera; a general 3D camera includes a first lens and a second lens, and images obtained by the two lenses are processed to obtain a corresponding 3D image. It should be noted that the specific type of the 3D sensor is not limited in the present disclosure. In theory, it is also possible to use a sensor capable of obtaining a plane image or depth information of an object in combination with an ordinary 2D sensor to obtain a function similar to that of a 3D sensor.

3) A Microcontroller Unit (MCU), also known as a Single Chip Microcomputer (SCM), is a chip-level computer formed by appropriately reducing frequency and specifications of a Central Process Unit (CPU), and integrating peripheral interfaces such as a memory, a Timer, a Universal Serial Bus (USB), an analog to digital converter (A/D), a Universal Asynchronous Receiver/Transmitter, and a Programmable Logic Controller (PLC), and even driving circuits of a Liquid Crystal Display (LCD) on a single chip, which provides control with different combinations for different application situations.

FIG. 1 is a schematic structural diagram of an application scenario according to the present disclosure. A system shown in FIG. 1 includes a 3D sensor 1, a Microcontroller Unit (MCU) 2, a memory 3, and an indicator 4. Specifically, the MCU 2 receives an initial image sent by the 3D sensor 1; the MCU 2 extracts a target corneal curvature from the initial image, then obtains a reference corneal curvature from the memory 3, compares the target corneal curvature with the reference corneal curvature, determines that a user is currently in a fatigue state if an absolute value of a difference between the target corneal curvature and the reference corneal curvature is greater than a preset threshold, and transmits a user reminding information to the indicator 4.

The technical solutions of the present disclosure and how the technical solutions of the present disclosure solve the technical problems described above will be described in detail below with reference to specific embodiments. The following specific embodiments may be combined with each other, and same or similar concepts or processes may not be repeated in some embodiments. Embodiments of the present disclosure are described below with reference to the drawings.

Figure 2:
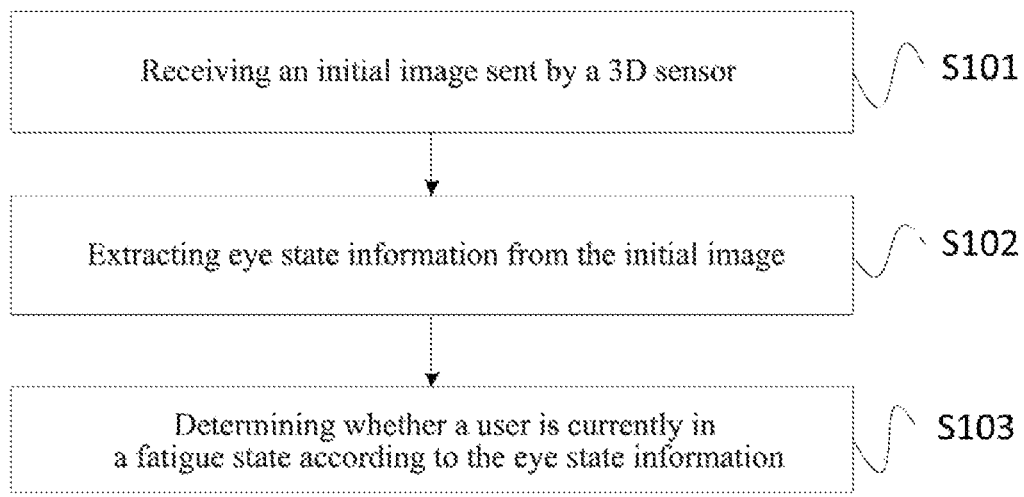
FIG. 2 is a flowchart of a method for detecting a fatigue state according to Embodiment I of the present disclosure.

FIG. 2 is a flowchart of a method for detecting a fatigue state according to Embodiment I of the present disclosure. As shown in FIG. 2, the method in this embodiment may include:

S101: receiving an initial image sent by a 3D sensor.

In practical application, an executive body of this embodiment may be a Microcontroller Unit (MCU), a Single Chip Microcomputer, a Microprocessor and other devices with a data processing capability. In this embodiment, an MCU is taken as an example for detailed description, but a specific type of the device for performing the method in this embodiment is not limited.

In this embodiment, an MCU may be integrated with a 3D sensor as one module, or may be a separate module electrically connected with the 3D sensor. Firstly, the MCU receives an initial image collected by the 3D sensor, where the initial image includes depth information containing an eye contour. A common 3D sensor includes a 3D camera; a general 3D camera includes a first lens and a second lens, and images acquired by the two lenses are processed to obtain a corresponding 3D image, or a structured-light 3D sensor or a 3D time-of-flight sensor can be used. It should be noted that a specific type of the 3D sensor is not limited in the present disclosure. In theory, it is also possible to use a sensor capable of acquiring a plane image or depth information of an object in combination with an ordinary 2D sensor to obtain a function similar to that of the 3D sensor. In this embodiment, the initial image sent by the 3D sensor may be a three-dimensional image or a two-dimensional image; when the initial image is a three-dimensional image, it includes depth information of the eye contour.

S102: extracting eye state information from the initial image.

In this embodiment, a first eye region image can be identified from the initial image sent by the 3D sensor; the first eye region image refers to an image including a binocular or monocular portion of a user, and the eye state information includes: blink times, total duration of closing eyes, duration of keeping eyes closed, and a corneal curvature. Optionally, the first eye region image at least includes: an image of a monocular eyelid or binocular eyelids, and an image of a pupil region.

Figure 3:
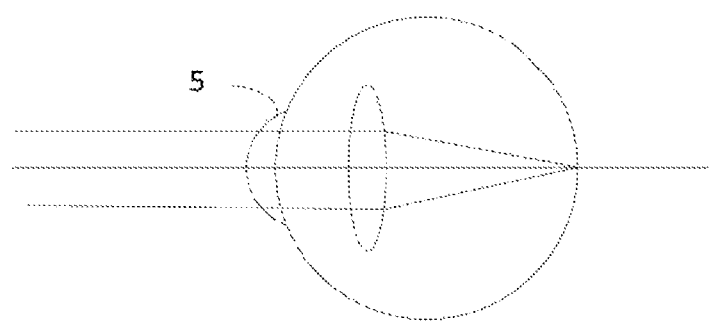
FIG. 3 is a schematic structural diagram of an eyeball when a human eye is in a normal state.
Figure 4:
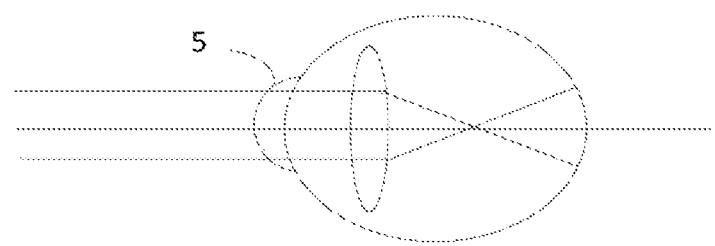
FIG. 4 is a schematic structural diagram of an eyeball when a human eye is in a fatigue state.

In one implementation, if an eyelid in the first eye region image is in an open state, the corneal curvature is extracted from the first eye region image. Specifically, extracting the corneal curvature needs contour depth information of a known eyeball region. At that time, the initial image sent by the 3D sensor needs to be a three-dimensional image, and the three-dimensional image contains the depth information of the eye contour, so that the MCU can obtain the corneal curvature according to the depth information of the contour of the eyeball region. Further, the MCU can also obtain information such as blink times, total duration of closing eyes, and duration of keeping eyes closed according to the three-dimensional image. FIG. 3 is a schematic structural diagram of an eyeball when a human eye is in a normal state, and FIG. 4 is a schematic structural diagram of an eyeball when a human eye is in a fatigue state. Referring to FIG. 3 and FIG. 4, it can be seen that the curvature of a cornea 5 can reflect whether the human eye is in the fatigue state.

In another implementation, the initial image sent by the 3D sensor may also be a two-dimensional image (where for example only one camera is turned on, or a 2D sensor therein is used to capture the initial image) if only information of blink times, total duration of closing eyes and duration of keeping eyes closed is required. At that time, the MCU can obtain information such as blink times, total duration of closing eyes, and duration of keeping eyes closed directly according to the two-dimensional image.

Optionally, if the eyelid in the first eye region image is in a closed state, a new initial image sent by the 3D sensor is received after waiting a first preset time; and a second eye region image is identified from the new initial image. It should be noted that the second eye region image in this embodiment refers to an image including a binocular or monocular portion of the user, which is different from the first eye region image in view of the different collecting time. Optionally, the second eye region image at least includes an image of the eyelid and an image of the pupil region. If the eyelid in the second eye region image is in the open state, the corneal curvature is extracted from the second eye region image; if the eyelid in the second eye region image is in the closed state, initial images of N frames within a second preset time range are continuously obtained according to a preset time interval, N being a natural number greater than 1; eye state information in the second preset time range is obtained from the initial images of N frames, where the eye state information includes: blink times, total duration of closing eyes, duration of keeping eyes closed, and the corneal curvature.

Optionally, if at least one of preset conditions is met within the second preset time range, it is determined that the user is currently in the fatigue state, where the preset conditions include:

blink times being not within a preset amount range;

total duration of closing eyes being greater than a first upper limit value;

duration of keeping eyes closed being greater than a second upper limit value; and an absolute value of a difference between a corneal curvature of an initial image of at least one frame in the initial images of N frames and a reference corneal curvature being greater than a preset threshold value.

S103: determining whether a user is currently in a fatigue state according to the eye state information.

In this embodiment, the target corneal curvature can be compared with a reference corneal curvature, and if an absolute value of a difference between the target corneal curvature and the reference corneal curvature is greater than a preset threshold, it is determined that the user is currently in the fatigue state. Optionally, the reference corneal curvature is a corneal curvature detected when the user is in a normal state, or is a pre-stored corneal curvature.

Optionally, the reference corneal curvature in different modes, for example, the reference corneal curvature in a driving mode, the reference corneal curvature in a night mode, the reference corneal curvature in a day mode, and the like, may be stored in a local memory of the MCU or a memory electrically connected to the MCU. Taking being in a driving mode as an example, curvature information of a user's eyes in a normal state is firstly obtained before a fatigue state detection is carried out on the user. The curvature information in the normal state may be data stored in history or data detected when the user just starts a vehicle. The way of obtaining the reference corneal curvature in the night mode and in the day mode is similar to that in the driving mode. Specifically, it is possible to determine whether it is currently at night or in the daytime from the brightness in the initial image collected by the 3D sensor.

Optionally, the reference corneal curvature in different modes can also be downloaded from the cloud. A source and a specific collection process of the reference corneal curvature are not limited in this embodiment.

Before step S101, or at any time during performing steps S101 to S103, following steps can be performed:

transmitting a control signal to the 3D sensor to enable the 3D sensor to collect the initial image according to a preset frequency.

In this embodiment, a frequency of collecting the initial image by the 3D sensor can be controlled by the MCU. For example, when the eye state information in M initial images continuously detected all indicates that the user is in a non-fatigue state, the frequency of collecting the initial images by the 3D sensor is reduced, M being a natural number greater than or equal to 1, and the value of M being adjustable according to an actual situation.

In this embodiment, by receiving an initial image sent by a 3D sensor where the initial image includes depth information containing an eye contour, extracting eye state information from the initial image, and determining whether a user is currently in a fatigue state according to the eye state information, detecting whether the user is in a fatigue state through the eye state information is thereby achieved, with high detection efficiency and more accurate detection results.

Figure 5:
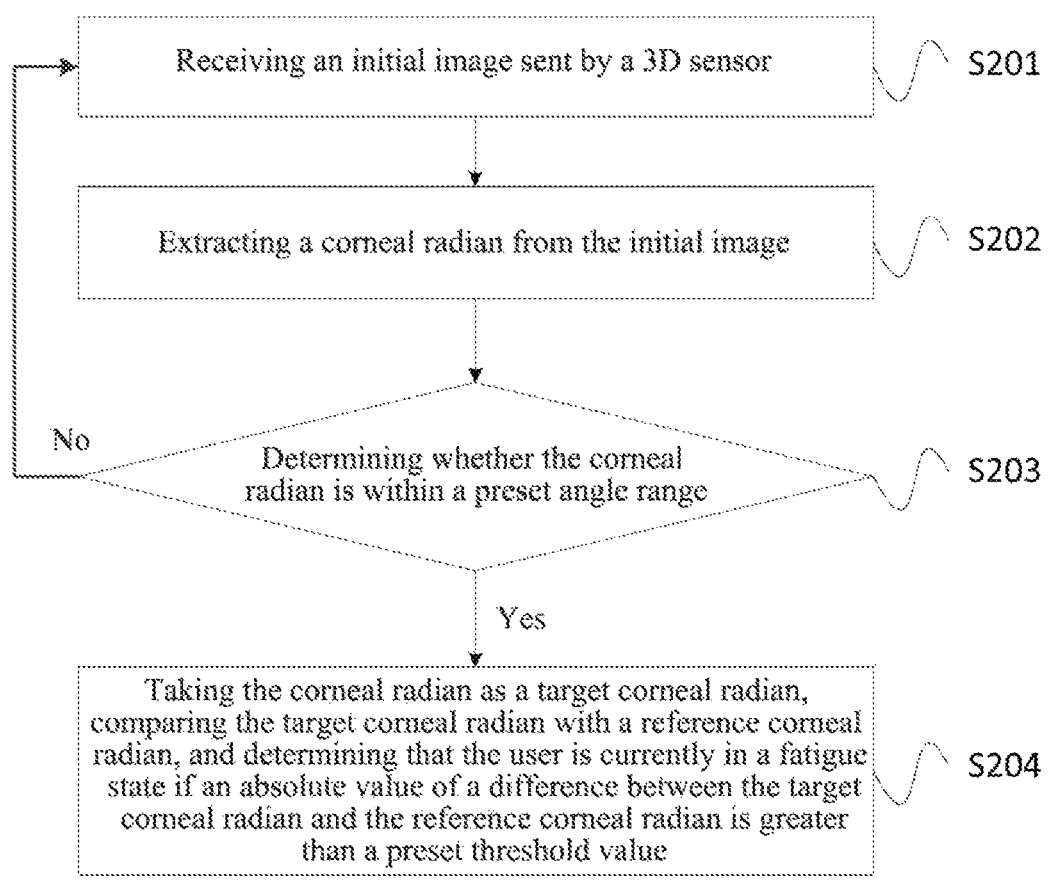
FIG. 5 is a flowchart of a method for detecting a fatigue state according to Embodiment II of the present disclosure.

FIG. 5 is a flowchart of a method for detecting a fatigue state according to Embodiment II of the present disclosure. As shown in FIG. 5, the method in this embodiment may include:

S201: receiving an initial image sent by a 3D sensor.

S202: extracting a corneal curvature from the initial image.

In this embodiment, for a specific implementation process and principles of steps S201 to S202, reference can be made to the related description in the method shown in FIG. 2, which will not be repeated herein.

S203: determining whether the corneal curvature is within a preset angle range, and if the corneal curvature is within the preset angle range, performing a step S204; if the corneal curvature is not within the preset angle range, determining the corneal curvature to be invalid data, and returning to perform the step S201.

In this embodiment, by filtering the corneal curvature extracted from the initial image to remove obviously abnormal data, such as data where the corneal curvature is not within the preset angle range, the influence of the invalid data on the detection results is thus eliminated, making the detection results more accurate.

S204: taking the corneal curvature as a target corneal curvature, comparing the target corneal curvature with a reference corneal curvature, and determining that the user is currently in a fatigue state if an absolute value of a difference between the target corneal curvature and the reference corneal curvature is greater than a preset threshold value.

In this embodiment, by receiving an initial image sent by a 3D sensor, where the initial image includes depth information containing an eye contour, extracting a corneal curvature from the initial image, then filtering the corneal curvature to remove invalid data not within a preset angle range and obtain a target corneal curvature, and determining whether a user is currently in a fatigue state according to the target corneal curvature, detecting whether the user is in a fatigue state through the corneal curvature is thereby achieved, with high detection efficiency and more accurate detection results.

Figure 6:
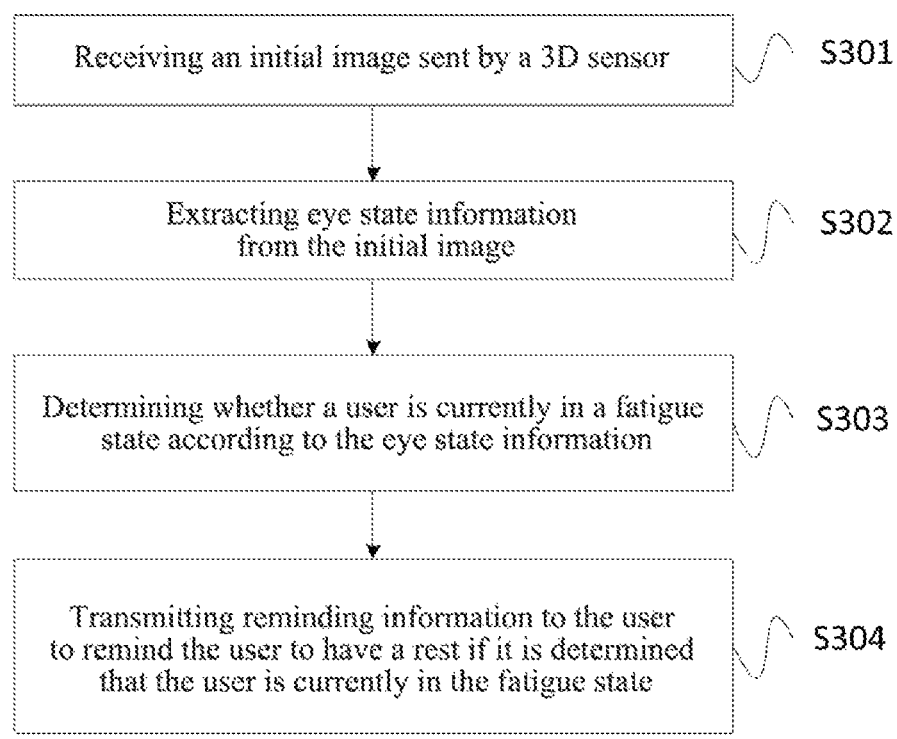
FIG. 6 is a flowchart of a method for detecting a fatigue state according to Embodiment III of the present disclosure.

FIG. 6 is a flowchart of a method for detecting a fatigue state according to Embodiment III of the present disclosure. As shown in FIG. 6, the method in this embodiment may include:

S301: receiving an initial image sent by a 3D sensor;

S302: extracting eye state information from the initial image;

S303: determining whether a user is currently in a fatigue state according to the eye state information.

In this embodiment, for a specific implementation process and principles of steps S301 to S303, reference can be made to the related description in the method shown in FIG. 2, which will not be repeated herein.

S304: transmitting reminding information to the user to remind the user to have a rest if it is determined that the user is currently in the fatigue state.

In this embodiment, the MCU is electrically connected with a display, a buzzer, a voice terminal and the like, and when it is determined that the user is currently in a fatigue state, a text reminder can be made through the display, and text contents are to remind the user to have a rest; or a reminder is sent to the user through the buzzer, or a voice reminder is made to the user through the voice terminal. It should be noted that specific reminding manners are not limited in this embodiment.

In this embodiment, by receiving an initial image sent by a 3D sensor, where the initial image includes depth information containing an eye contour, extracting eye state information from the initial image, determining whether a user is currently in a fatigue state according to the eye state information, and transmitting reminding information to the user to remind the user to have a rest when it is determined that the user is currently in the fatigue state, detecting whether a user is in a fatigue state through the eye state information is thereby achieved, with high detection efficiency and more accurate detection results, and timely reminder can be given when the user is in the fatigue state.

Figure 7:
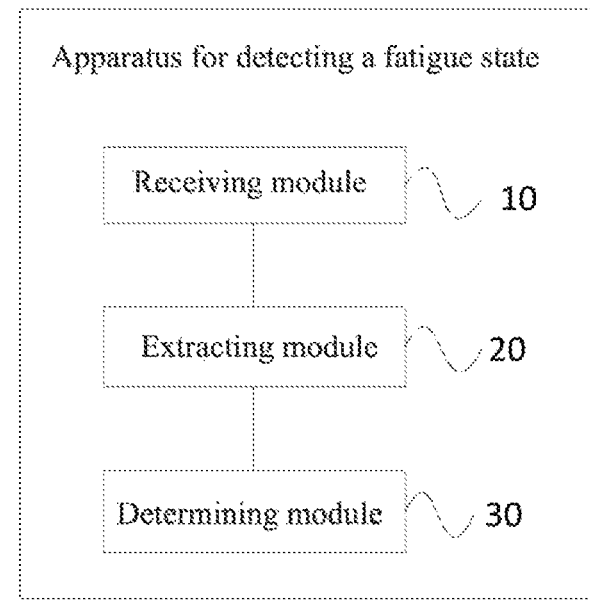
FIG. 7 is a schematic structural diagram of an apparatus for detecting a fatigue state according to Embodiment IV of the present disclosure.

FIG. 7 is a schematic structural diagram of an apparatus for detecting a fatigue state according to Embodiment IV of the present disclosure. As shown in FIG. 7, the apparatus in this embodiment can include:

a receiving module 10, configured to receive an initial image sent by a 3D sensor;

an extracting module 20, configured to extract eye state information from the initial image; and a determining module 30, configured to determine whether a user is currently in a fatigue state according to the eye state information.

Optionally, the extracting module 20 is specifically configured to:

identify a first eye region image from the initial image; and extract a corneal curvature from the first eye region image if an eyelid in the first eye region image is in an open state.

Optionally, the extracting module 20 is further configured to:

receive a new initial image sent by the 3D sensor after waiting a first preset time, if the eyelid in the first eye region image is in a closed state;

identify a second eye region image from the new initial image;

extract a corneal curvature from the second eye region image if an eyelid in the second eye region image is in an open state;

continuously obtain initial images of N frames within a second preset time range according to a preset time interval, if the eyelid in the second eye region image is in a closed state, N being a natural number greater than 1; and obtain eye state information in the second preset time range from the initial images of N frames, where the eye state information includes: blink times, total duration of closing eyes, duration of keeping eyes closed, and a corneal curvature.

Optionally, the determining module 30 is specifically configured to:

compare a target corneal curvature with a reference corneal curvature, and determine that a user is currently in a fatigue state if an absolute value of a difference between the target corneal curvature and the reference corneal curvature is greater than a preset threshold value.

Optionally, the reference corneal curvature is a corneal curvature detected when a user is in a normal state, or is a pre-stored corneal curvature.

Optionally, the determining module 30 is further configured to:

determine that a user is currently in a fatigue state if at least one of preset conditions is met within the second preset time range, where the preset conditions include:

blink times being not within a preset amount range;

total duration of closing eyes being greater than a first upper limit value;

duration of keeping eyes closed being greater than a second upper limit value; and an absolute value of a difference between a corneal curvature of an initial image of at least one frame in the initial images of N frames and the reference corneal curvature being greater than a preset threshold value.

The apparatus in this embodiment can perform the method shown in FIG. 2, and for a specific implementation process and technical principles thereof, reference can be made to the related description in the method shown in FIG. 2, which will not be repeated herein.

Figure 8:
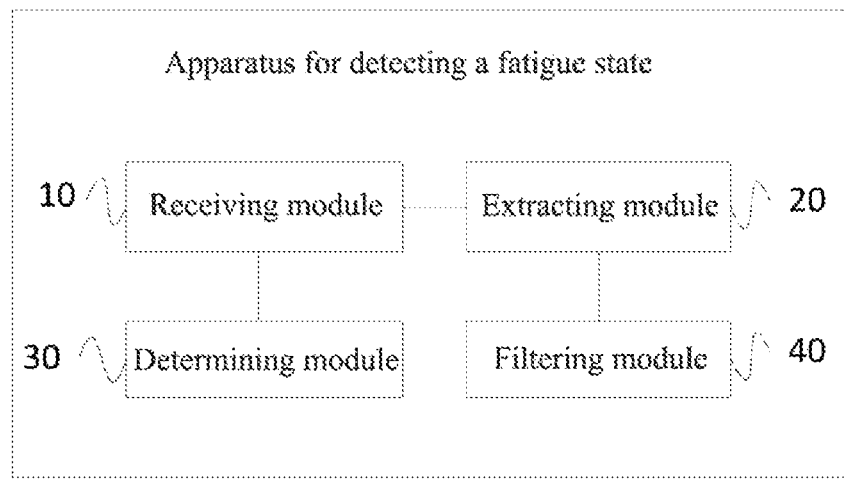
FIG. 8 is a schematic structural diagram of an apparatus for detecting a fatigue state according to Embodiment V of the present disclosure.

FIG. 8 is a schematic structural diagram of an apparatus for detecting a fatigue state according to Embodiment V of the present disclosure. As shown in FIG. 8, on the basis of the apparatus shown in FIG. 7, the apparatus in this embodiment may further include:

a filtering module 40, configured to determine whether the corneal curvature is within a preset angle range before the determining whether the user is currently in the fatigue state according to the eye state information, take the corneal curvature as a target corneal curvature if the corneal curvature is within the preset angle range, and determine the corneal curvature to be invalid data and receive again an initial image sent by the 3D sensor, if the corneal curvature is not within the preset angle range.

The apparatus in this embodiment can perform the method shown in FIG. 5, and for a specific implementation process and technical principles thereof, reference can be made to the related description in the method shown in FIG. 5, which will not be repeated herein.

Figure 9:
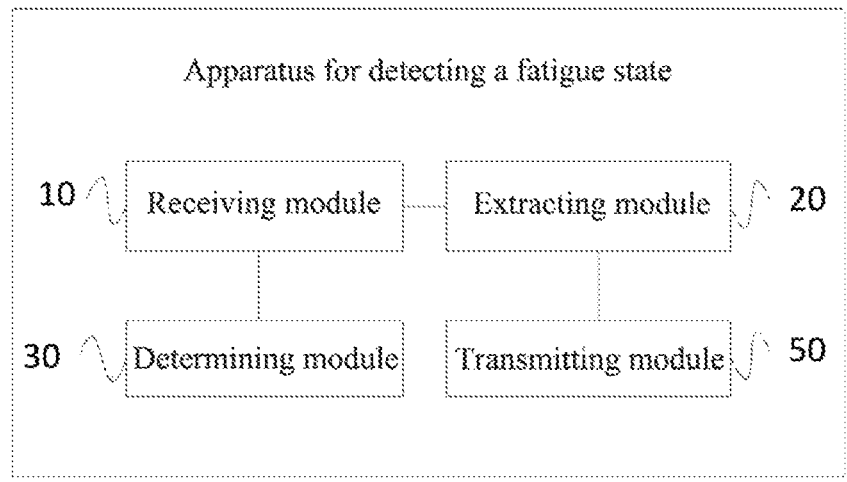
FIG. 9 is a schematic structural diagram of an apparatus for detecting a fatigue state according to Embodiment VI of the present disclosure.

FIG. 9 is a schematic structural diagram of an apparatus for detecting a fatigue state according to Embodiment VI of the present disclosure. As shown in FIG. 9, on the basis of the apparatus shown in FIG. 7, the apparatus in this embodiment may further include:

a transmitting module 50, configured to transmit a control signal to a 3D sensor before an initial image sent by the 3D sensor is received, so that the 3D sensor collects the initial image at a preset frequency.

Optionally, the transmitting module 50 is further configured to, after whether the user is currently in a fatigue state is determined according to the eye state information, transmit reminding information to the user to remind the user to have a rest if it is determined that the user is currently in the fatigue state.

The apparatus in this embodiment can perform the method shown in FIG. 6, and for a specific implementation process and technical principles thereof, reference can be made to the related description in the method shown in FIG. 6, which will not be repeated herein.

Figure 10:
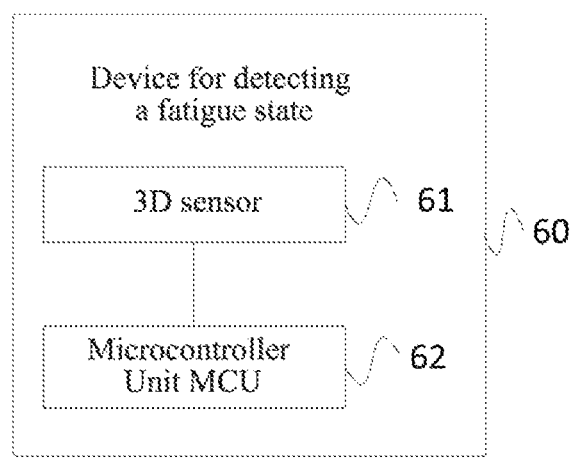
FIG. 10 is a schematic structural diagram of a device for detecting a fatigue state according to Embodiment VII of the present disclosure.

FIG. 10 is a schematic structural diagram of a device for detecting a fatigue state according to Embodiment VII of the present disclosure. A device 60 shown in FIG. 10 includes a 3D sensor 61 and a Microcontroller Unit (MCU) 62, where the 3D sensor 61 is electrically connected to the MCU 62;

The 3D sensor 61 is configured to collect an initial image and transmit the initial image to the MCU.

The MCU 62 is configured to perform the method for detecting a fatigue state as described in any one of FIG. 2, FIG. 5 and FIG. 6.

Figure 11:
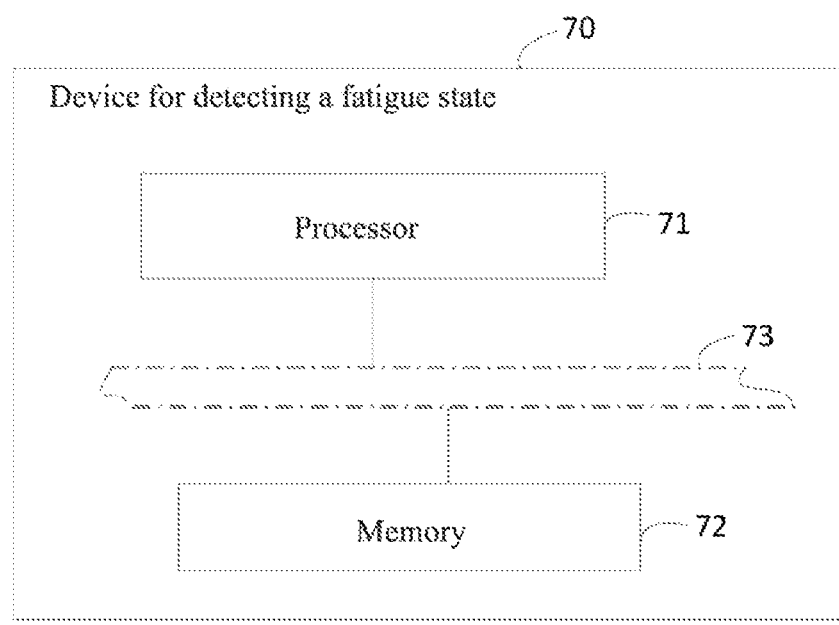
FIG. 11 is a schematic structural diagram of a device for detecting a fatigue state according to Embodiment VIII of the present disclosure.

FIG. 11 is a schematic structural diagram of a device for detecting a fatigue state according to Embodiment VIII of the present disclosure. As shown in FIG. 11, a fatigue state detection device 70 in this embodiment includes:

a processor 71 and a memory 72, where the memory 72 is configured to store executable instructions, where the memory may also be a flash; and the processor 71 is configured to execute the executable instructions stored in the memory to implement various steps in the method involved in the above embodiments. For details, reference can be made to the related description in the foregoing method embodiments.

Optionally, the memory 72 may be independent or be integrated with the processor 71.

When the memory 72 is a device independent of the processor 71, the fatigue state detection device 70 may further include:

a bus 73, configured to connect the memory 72 with the processor 71.

In addition, embodiments of the present disclosure further provide a computer readable storage medium, the computer readable storage medium stores computer executive instructions, and when at least one processor of a user equipment executes the computer executive instructions, the user equipment performs the foregoing various possible methods.

Here, the computer readable medium includes a computer storage medium and a communication medium, where the communication medium includes any medium that facilitates the transfer of a computer program from one place to another. The storage medium may be any available medium that can be accessed by general-purpose or dedicated computers. An exemplary storage medium is coupled to a processor to enable the processor to read information from, and write information to, the storage medium. Of course, the storage medium can also be a part of the processor. The processor and the storage medium may be located in an application-specific integrated circuit (ASIC). Additionally, the application-specific integrated circuit can be located in a user equipment. Of course, the processor and the storage medium may also be located in a communication device as discrete components.

Persons of ordinary skill in the art will appreciate that all or part of the steps for implementing the above various method embodiments may be accomplished by a program instruction related hardware. The above program can be stored in a computer readable storage medium. The program, when executed, performs the steps including the foregoing method embodiments; and the foregoing storage medium includes various media that can store a program code, such as a read only memory (ROM), a random access memory (RAM), a magnetic disk, or an optical disk.

After considering the specification and practicing the disclosure disclosed herein, those skilled in the art will easily come up with other embodiments of the present disclosure. The present disclosure is intended to cover any variations, uses, or adaptive changes of the present disclosure, and these variations, uses, or adaptive changes follow the general principles in the present disclosure and include common knowledge or common technical means in the art that are not disclosed in the present disclosure. The specification and embodiments are to be regarded as illustrative only and the true scope and spirit of the present disclosure are indicated in the claims below.

It is to be understood that the present disclosure is not limited to the exact structure described above and shown in the appended drawings, and can be modified and changed in a variety of ways without departing from its scope. The scope of the present disclosure is limited only by the accompanying claims.

What is claimed is:

1. A method for detecting a fatigue state, comprising:
receiving an initial image sent by a 3D sensor;
extracting eye state information from the initial image; and
determining whether a user is currently in the fatigue state according to the eye state information;
wherein the extracting eye state information from the initial image comprises:
identifying a first eye region image from the initial image; and extracting a corneal curvature from the first eye region image as the eye state information, if an eyelid in the first eye region image is in an open state;

wherein the determining whether a user is currently in the fatigue state according to the eye state information comprises:

comparing the corneal curvature with a reference corneal curvature, and determining that the user is currently in the fatigue state if an absolute value of a difference between the corneal curvature and the reference corneal curvature is greater than a preset threshold value.

2. The method according to claim 1, wherein after identifying the first eye region image from the initial image, the method further comprises:

receiving a new initial image sent by the 3D sensor after waiting a first preset time, if the eyelid in the first eye region image is in a closed state;

identifying a second eye region image from the new initial image; and extracting the corneal curvature from the second eye region image if the eyelid in the second eye region image is in the open state.

3. The method according to claim 2, further comprising: continuously obtaining initial images of N frames within a second preset time range according to a preset time interval, if the eyelid in the second eye region image is in the closed state, N being a natural number greater than 1; and obtaining eye state information within the second preset time range from the initial images of N frames, wherein the eye state information comprises: blink times, total duration of closing eyes, duration of keeping eyes closed, and the corneal curvature.

4. The method according to claim 1, wherein before the determining whether a user is currently in the fatigue state according to the eye state information, the method further comprises:

determining whether the corneal curvature is within a preset angle range, and if the corneal curvature is within the preset angle range, taking the corneal curvature as a target corneal curvature;

if the corneal curvature is not within the preset angle range, determining the corneal curvature to be invalid data, and receiving an initial image sent by the 3D sensor again.

5. The method according to claim 4, wherein the determining whether a user is currently in the fatigue state according to the eye state information comprises:

comparing the target corneal curvature with the reference corneal curvature, and determining that the user is currently in the fatigue state if an absolute value of a difference between the target corneal curvature and the reference corneal curvature is greater than a preset threshold value.

6. The method according to claim 1, wherein the reference corneal curvature is a corneal curvature detected when the user is in a normal state, or is a pre-stored corneal curvature.

7. The method according to claim 3, wherein the determining whether the user is currently in the fatigue state according to the eye state information further comprises:

determining that the user is currently in the fatigue state if at least one of preset conditions is met within the second preset time range, wherein the preset conditions comprise:

the blink times being not within a preset amount range;

the total duration of closing eyes being greater than a first upper limit value;

the duration of keeping eyes closed being greater than a second upper limit value; and an absolute value of a difference between a corneal curvature of an initial image of at least one frame in the initial images of N frames and a reference corneal curvature being greater than a preset threshold value.

8. The method according to claim 1, wherein before receiving an initial image sent by a 3D sensor, the method further comprises:

transmitting a control signal to the 3D sensor to enable the 3D sensor to collect the initial image at a preset frequency.

9. The method according to claim 1, wherein after determining whether a user is currently in the fatigue state according to the eye state information, the method further comprises:

transmitting reminding information to the user to remind the user to have a rest if it is determined that the user is currently in the fatigue state.

10. An apparatus for detecting a fatigue state, comprising a processor and a memory, wherein the processor is configured to execute program instructions stored in the memory to:

receive an initial image sent by a 3D sensor;

extract eye state information from the initial image; and determine whether a user is currently in the fatigue state according to the eye state information;

wherein the processor is further configured to:

identify a first eye region image from the initial image and extract a corneal curvature from the first eye region image as the eye state information, if an eyelid in the first eye region image is in an open state; and compare the corneal curvature with a reference corneal curvature, and determine that the user is currently in the fatigue state if an absolute value of a difference between the corneal curvature and the reference corneal curvature is greater than a preset threshold value.

11. A device for detecting a fatigue state, comprising: a 3D sensor and a Microcontroller Unit (MCU), wherein the 3D sensor is electrically connected with the Microcontroller Unit (MCU);

the 3D sensor is configured to collect an initial image and transmit the initial image to the MCU; and the MCU is configured to:

receive the initial image;

extract eye state information from the initial image; and determine whether a user is currently in the fatigue state according to the eye state information;

wherein the MCU is further configured to:

identify a first eye region image from the initial image and extract a corneal curvature from the first eye region image as the eye state information, if an eyelid in the first eye region image is in an open state; and compare the corneal curvature with a reference corneal curvature, and determine that the user is currently in the fatigue state if an absolute value of a difference between the corneal curvature and the reference corneal curvature is greater than a preset threshold value.

12. The device according to claim 11, wherein the MCU is further configured to:

receive a new initial image sent by the 3D sensor after waiting a first preset time, if the eyelid in the first eye region image is in a closed state;

identify a second eye region image from the new initial image;

extract the corneal curvature from the second eye region image if the eyelid in the second eye region image is in the open state; and continuously obtain initial images of N frames within a second preset time range according to a preset time interval, if the eyelid in the second eye region image is in the closed state, N being a natural number greater than 1, and obtain eye state information within the second preset time range from the initial images of N frames, wherein the eye state information comprises: blink times, total duration of closing eyes, duration of keeping eyes closed, and the corneal curvature.

13. The device according to claim 12, wherein the MCU is further configured to:

determine that the user is currently in the fatigue state if at least one of preset conditions is met within the second preset time range, wherein the preset conditions comprise:

the blink times being not within a preset amount range;

the total duration of closing eyes being greater than a first upper limit value;

the duration of keeping eyes closed being greater than a second upper limit value; and an absolute value of a difference between a corneal curvature of an initial image of at least one frame in the initial images of N frames and a reference corneal curvature being greater than a preset threshold value.

14. The device according to claim 11, wherein the MCU is further configured to:

determine whether the corneal curvature is within a preset angle range before determining whether the user is currently in the fatigue state according to the eye state information, take the corneal curvature as a target corneal curvature if the corneal curvature is within the preset angle range, and determine the corneal curvature to be invalid data, and receive again an initial image sent by the 3D sensor, if the corneal curvature is not within the preset angle range.

15. The device according to claim 14, wherein the MCU is further configured to:

compare the target corneal curvature with the reference corneal curvature, and determine that the user is currently in the fatigue state if an absolute value of a difference between the target corneal curvature and the reference corneal curvature is greater than a preset threshold value.

16. The device according to claim 11, wherein the reference corneal curvature is a corneal curvature detected when the user is in a normal state, or is a pre-stored corneal curvature.

17. The device according to claim 11, the MCU is further configured to:

transmit a control signal to the 3D sensor to make the 3D sensor collects the initial image at a preset frequency.

18. The device according to claim 11, wherein the MCU is further configured to transmit reminding information to the user to remind the user to have a rest if it is determined that the user is currently in a fatigue state according to the eye state information.

* * * * *